United States Patent
Ortiz et al.

(10) Patent No.: US 7,354,767 B2
(45) Date of Patent: Apr. 8, 2008

(54) REFERENCE CONTROL COMPOSITION CONTAINING A NUCLEATED RED BLOOD CELL COMPONENT MADE OF NON-NUCLEATED BLOOD CELLS

(75) Inventors: Nery Ortiz, Miami, FL (US); Theodore J. Gerula, Fort Lauderdale, FL (US); Sandra Socarras, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 12 days.

(21) Appl. No.: 11/377,171

(22) Filed: Mar. 16, 2006

(65) Prior Publication Data

US 2007/0218558 A1      Sep. 20, 2007

(51) Int. Cl.
*G01N 33/48* (2006.01)
*G01N 31/00* (2006.01)

(52) U.S. Cl. .............. 436/10; 436/8; 436/17; 436/63; 436/149; 436/150; 436/164; 436/166; 436/174; 436/176; 435/2

(58) Field of Classification Search .......... 436/8, 436/10, 17, 63, 149, 150, 164, 166, 174, 436/176; 435/2
See application file for complete search history.

(56) References Cited

U.S. PATENT DOCUMENTS

| | | | |
|---|---|---|---|
| 3,873,467 A | 3/1975 | Hunt | |
| 4,213,876 A | 7/1980 | Crews et al. | |
| 4,264,470 A | 4/1981 | Chastain, Jr. et al. | |
| 4,299,726 A | 11/1981 | Crews et al. | |
| 4,358,394 A | 11/1982 | Crews et al. | |
| 4,389,490 A | 6/1983 | Crews et al. | |
| 4,405,719 A | 9/1983 | Crews et al. | |
| 4,704,364 A | 11/1987 | Carver et al. | |
| 4,735,504 A * | 4/1988 | Tycko ......................... 356/336 | |
| 5,125,737 A | 6/1992 | Rodriguez et al. | |
| 5,320,964 A | 6/1994 | Young et al. | |
| 5,512,485 A | 4/1996 | Young et al. | |
| 5,559,037 A | 9/1996 | Kim et al. | |
| 5,858,790 A | 1/1999 | Kim et al. | |
| 5,874,310 A | 2/1999 | Li et al. | |
| 5,879,900 A | 3/1999 | Kim et al. | |
| 5,917,584 A | 6/1999 | Li et al. | |
| 6,060,322 A | 5/2000 | Horton et al. | |
| 6,187,590 B1 | 2/2001 | Kim et al. | |
| 6,200,500 B1 | 3/2001 | Ryan | |
| 6,221,668 B1 | 4/2001 | Ryan et al. | |
| 6,399,388 B1 | 6/2002 | Ryan et al. | |
| 6,403,377 B1 | 6/2002 | Ryan et al. | |
| 6,406,915 B2 | 6/2002 | Ryan et al. | |
| 6,410,330 B1 | 6/2002 | Li et al. | |
| 6,448,085 B1 | 9/2002 | Wang et al. | |
| 6,472,215 B1 | 10/2002 | Huo et al. | |
| 6,569,682 B2 | 5/2003 | Elliott et al. | |
| 6,653,137 B2 | 11/2003 | Ryan | |
| 6,673,618 B1 | 1/2004 | Li et al. | |
| 6,723,563 B2 | 4/2004 | Ryan | |
| 7,195,919 B2 * | 3/2007 | Jacobs et al. ................. 436/10 |
| 2005/0136409 A1 | 6/2005 | Jacobs et al. | |
| 2007/0072298 A1 * | 3/2007 | Ortiz et al. .................. 436/16 |

* cited by examiner

*Primary Examiner*—Maureen M. Wallenhorst
(74) *Attorney, Agent, or Firm*—Cuspa Technology Law Associates; Mitchell E. Alter

(57) ABSTRACT

A reference control composition containing a nucleated red blood cell component and the method of making are disclosed. The reference control composition includes a nucleated red blood cell component made of fixed non-nucleated blood cells and a suspension medium. The non-nucleated blood cell has a natural cell size substantially similar to a size of nucleus of said nucleated red blood cell of said blood sample. The nucleated red blood cell component can be made of equine, ovine, bovine, feline, canine, or porcine red blood cells; and it is substantially free of nucleic acid. The reference control composition can further include a white blood cell component, a red blood cell component, a platelet component, a reticulocyte component, or combinations thereof. Further disclosed are the methods of using the reference control composition for measurement of nucleated red blood cells on a blood analyzer.

25 Claims, 3 Drawing Sheets

REFERENCE CONTROL COMPOSITION CONTAINING A NUCLEATED RED BLOOD CELL COMPONENT MADE OF NON-NUCLEATED BLOOD CELLS

FIELD OF THE INVENTION

The present invention relates to a reference control composition containing a nucleated red blood cell component and the method of making and using the reference control composition for determination of nucleated red blood cells of a blood sample on a blood analyzer.

BACKGROUND OF THE INVENTION

Quality control has long been a necessary and routine procedure in clinical hematology. Accuracy in the counting of various types of blood cells is dependent, in part, upon the use of adequate control products and methods of using the control products. With the numerous types of equipment for particle counting now available, quality control by the use of control products is necessary, since the possibility of an instrument malfunctioning is ever present. The traditional method of maintaining a quality control program for automatic particle counting equipment has consisted of providing fresh human blood as a whole blood standard. However, this fresh blood is usable for only one day, therefore, various manufactured control products which have longer product lifetime have been developed.

Commonly used particles in a control product simulate or approximate the types of particles or cells that are intended to undergo analysis. Consequently, these particles have been frequently referred to as analog particles. The analog particles should be selected or designed so that they have certain characteristics that are similar to those of the particles or cells to be analyzed in the instruments. Exemplary characteristics and parameters include similarities in size, volume, surface characteristics, granularity properties, light scattering properties and fluorescence properties.

Various commercial reference control products are now available, which use various processed or fixed human or animal blood cells as analogs of human blood cells. U.S. Pat. No. 5,512,485 (to Young et al) teaches a hematology control comprising several white blood cell analogs made of processed and fixed animal nucleated red blood cells. Commercially available hematology controls can also contain red blood cell, platelet, reticulocyte and nucleated red blood cell components, and many of them are made of cellular analogs.

Nucleated red blood cells (NRBCs), or erythroblasts, are immature red blood cells. They are normally present in the bone marrow but not in peripheral blood. However, in certain diseases such as anemia and leukemia, nucleated red blood cells also present in peripheral blood. Therefore, it is of clinical importance to measure NRBCs. In recent years, several detection methods for measuring nucleated red blood cells in a blood sample on a hematology instrument have been reported. U.S. Pat. No. 5,559,037 (to Kim et al.) discloses a method for flow cytometric analysis of nucleated red blood cells and leukocytes. The method uses fluorescence, low angle light scatter and axial light loss measurements to differentiate NRBCs from white blood samples. U.S. Pat. No. 5,879,900 (to Kim et al) further discloses a method of differentiating NRBCs, white blood cells and damaged white blood cells, and providing a white blood cell differential in a blood sample by flow cytometry.

U.S. Pat. Nos. 5,874,310 and 5,917,584 (to Li et al) disclose a method of differentiating nucleated red blood cells by measuring two angles of light scatter signals of a blood sample, and further disclose a method of differentiating nucleated red blood cells by measuring light scatter and DC impedance signals. U.S. Pat. Nos. 6,410,330 and 6,673,618 (to Li et al) disclose a method of determining NRBC by using DC impedance measurement. U.S. Pat. No. 6,472,215 (to Huo et al) discloses a method of differentiating nucleated red blood cells by an impedance measurement in combination with a three dimensional DC, RF and light scatter measurements.

With the development of detection methods for nucleated red blood cells, several hematology controls containing a nucleated red blood cell component, or NRBC analog, have been reported.

U.S. Pat. Nos. 6,187,590 and 5,858,790 (to Kim et al) disclose a hematology control comprising a nucleated red blood cell (NRBC) analog made of lysed and fixed avian or fish red blood cells, or lysed and fixed human lymphocytes. U.S. Pat. Nos. 6,187,590 and 5,858,790 further disclose the method of preparing the NRBC analog, by lysing avian or fish red blood cells with a lysing reagent for 1 to 5 minutes, followed by fixing remaining nuclei with a fixative at 60 to 70° C. for up to 10 minutes.

U.S. Pat. Nos. 6,406,915, 6,403,377, 6,399,388, 6,221,668 and 6,200,500 (to Ryan, et al) disclose a hematology control comprising a NRBC analog derived from nucleated avian blood cells. The method includes washing avian red blood cells, such as turkey or chicken red blood cells in a buffer solution and fixing the washed cells with glutaraldehyde phosphate solution. U.S. Pat. No. 6,448,085 (to Wang et al) discloses a hematology control comprising a nucleated red blood cell (NRBC) analog which is fixed nucleated chicken red blood cells obtained from a commercial source.

U.S. Pat. Nos. 6,653,137 and 6,723,563 (to Ryan) disclose methods of making a nucleated red blood cell component for a hematology control by stabilizing blood cells containing a nucleus; or by lysing and removing cytoplasm from the nucleated blood cells but preserving the general structure of the membrane about the nucleus, then fixing the treated nucleated blood cells.

All above-mentioned references teach of using nucleated blood cells to make the nucleated red blood cell component for a reference control for the measurement of nucleated red blood cells in a blood sample.

U.S. Patent Application Publication No. 2005/0136409 (to Jacobs et al) discloses a hematology control containing a nucleated red blood cell component and methods of making the same. The control comprises a particle, such as a non-fixed horse, sheep or bovine cell, having nucleic acids (DNA or RNA) attached to the surface of the particle for simulating a nucleated red blood cell. The method teaches covalently cross-linking RNA to the surface of the non-fixed red blood cell, wherein the red blood cells can be either nucleated or non-nucleated cells. The RNA-coated non-nucleated red blood cells can be used for measurement of nucleated red blood cells using fluorescence measurement. Jacobs et al. further disclose that the NRBC analogs made of RNA-coated horse red blood cells can be measured by impedance and light scatter measurements.

Furthermore, certain non-nucleated red blood cells, such as human, turkey, and shark red blood cells, have been used for making analogs of white blood cell subpopulations for hematology reference controls, such as those described in U.S. Pat. No. 4,704,364.

It is desirable to be able to use a broad range of blood cell sources for making the NRBC analog, particularly using those readily available non-nucleated blood cells.

SUMMARY OF THE INVENTION

In one aspect, the present invention is directed to a reference control composition containing a nucleated red blood cell component comprising a nucleated red blood cell component made of a fixed non-nucleated blood cell for simulating a nucleated red blood cell of a blood sample; and a suspension medium suitable for delivering the component to a blood analyzer for measurement of the nucleated red blood cell. The non-nucleated blood cell has a natural cell size substantially similar to a size of nucleus of the nucleated red blood cell of the blood sample to be measured. The non-nucleated blood cell suitable for the purpose of the present invention includes equine, ovine, bovine, feline, canine, porcine red blood cells or combinations thereof. Furthermore, the nucleated red blood cell component is substantially free of nucleic acid.

Moreover, the reference control composition can further comprise white blood cell, red blood cell, platelet and reticulocyte components.

In a further aspect, the present invention is directed to a method of making a reference control composition containing a nucleated red blood cell component. The method comprises the steps of providing a non-nucleated blood cell which has a natural cell size substantially similar to a size of a nucleus of a nucleated red blood cell to be measured; fixing the non-nucleated blood cell with a fixation medium; and suspending fixed non-nucleated blood cell in a suspension medium to form a reference control composition. The method can further comprise contacting the non-nucleated blood cell with a sphering reagent to sphere the non-nucleated blood cell prior to fixing.

In another aspect, the present invention is directed to a method of using the reference control composition for measurement of the nucleated red blood cells. The method comprises the steps of providing a reference control composition containing a nucleated red blood cell component made of a fixed non-nucleated blood cell for simulating a nucleated red blood cell of a blood sample to be measured; providing a blood analyzer adapted for measurement of the nucleated red blood cell of the blood sample; analyzing the reference control composition on the blood analyzer, and measuring the nucleated red blood cell component; and reporting the nucleated red blood cell component in the reference control composition. Herein, measuring the nucleated red blood cell component can be performed by measuring a DC impedance signal; measuring two angles of light scatter signals; measuring DC impedance and light scatter signals; measuring axial light loss and DC impedance signals; or measuring axial light loss and light scatter signals. The two angles of light scatter signals can be both low angle light scatter signals detected in less than 10°, or one low angle light scatter signal and one medium angle or right-angle light scatter signal. Furthermore, measuring the nucleated red blood cell component can be performed by measuring a first DC impedance signal of a first aliquot of the blood sample and measuring a second DC impedance signal, a radio frequency impedance signal, and a light scatter signal of a second aliquot of the blood sample.

DETAILED DESCRIPTION OF THE INVENTION

Figure 1A:
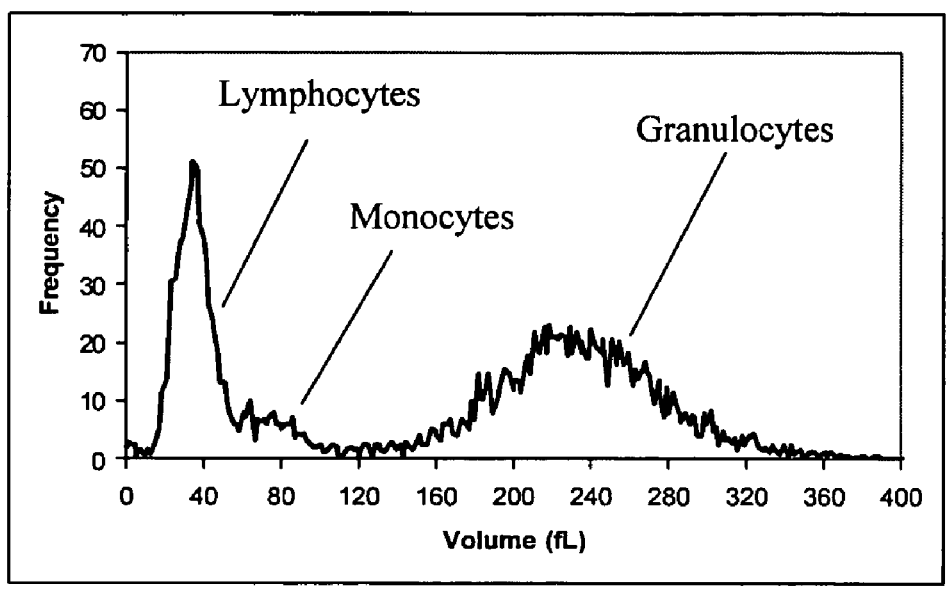
FIG. 1A shows a DC histogram of a normal blood sample analyzed according to the procedure described in Example 3.

In one aspect the present invention provides a reference control composition that contains a nucleated red blood cell (NRBC) component, and a method of preparing the nucleated red blood cell component and the reference control composition.

More specifically, in one embodiment the reference control composition comprises a nucleated red blood cell component made of a fixed non-nucleated blood cell for simulating nucleated red blood cells of a blood sample; and a suspension medium suitable for delivering the component to a blood analyzer for measurement of the nucleated red blood cells. For the purpose of the present invention, the nucleated red blood cell component, as well as other cell type components, is also referred to as analog, for example, NRBC analog.

Suitable non-nucleated blood cells should have a natural cell size substantially similar to the size of the nucleus of the nucleated red blood cells to be simulated. Upon processing by the method described hereinafter, the size of the non-nucleated blood cells can be further adjusted to simulate the nucleated red blood cells. Non-nucleated blood cells suitable for simulating the nucleated red blood cells include various animal non-nucleated red blood cells including, but are not limited to, equine, ovine, bovine, feline, canine, porcine red blood cells, or combinations thereof.

Nucleated red blood cells of a blood sample are usually measured together with white blood cells on a blood analyzer under a lysing condition. The blood sample is mixed with a lytic reagent to lyse abundant mature red blood cells. Under the lysing condition, the mature red blood cells are completely lysed; while the cellular membrane of the nucleated red blood cells is damaged and the cytoplasm is substantially released. The remaining portions of the nucleated red blood cells, which are mainly the nucleus and potentially the damaged cellular membrane depending on the lytic reagent used, are measured by various known detection methods. At this stage, the size of the nucleated red blood cell is essentially the size of the nucleus.

The natural cell size of non-nucleated blood cells can be determined on a blood analyzer by suspending the cells in an isotonic blood diluent, and measuring the cells by a direct current (DC) impedance measurement, or a low angle light scatter measurement. The term "natural cell size" used herein refers to the cell size substantially in its natural state, without being treated in vitro, except being in contact with anticoagulant during the blood collection, and in contact with an isotonic diluent during the measurement.

The nucleated red blood cell component made of non-nucleated blood cells can be produced by the following process:

(1) collect an amount of whole blood which contains non-nucleated red blood cells that have a natural cell size substantially similar to the size of the nucleus of a nucleated red blood cell to be simulated;

(2) separate the non-nucleated red blood cells from other cell components (including white blood cells, platelets, and plasma) by centrifuge;

(3) wash the packed cells with a washing solution;

(4) fix the non-nucleated blood cells with a fixation medium;

(5) wash the fixed non-nucleated blood cells with the wash solution; and (6) suspend the fixed non-nucleated blood cells in a suitable suspension medium to form a reference control composition for analysis on a blood analyzer.

One suitable wash solution is the phosphate buffered saline solution (PBS). Other wash solution known to those skilled in the art can also be used. Furthermore, a sphering agent can be added in the wash solution for sphering the non-nucleated blood cells prior to the fixation. Alternatively, the washed blood cells can be treated by a separate sphering reagent before fixation. Suitable examples of sphering agents include, but are not limited to, anionic surfactants including ammonium perfluoralkyl carboxylate (commercially available as Fluorad™ FC-143, 3M Company, St. Paul, Minn.), sodium lauroyl myristoyl lactylate (commercially available as Pationic™ 138C, R.I.T.A Corp, Woodstock, Ill.); non-ionic surfactants including dodecyl-β-D-maltoside, N,N-bis-(3-D-gluconamidopropyl)cholamide, polyoxypropylene-polyoxyethylene block copolymer, N-tetradecyl-β-D-maltoside, daconyl-N-methyl-glucamide, n-dodecyl-β-D-glucopyranoside, n-decyl-β-D-glucopyranoside, polyethylene glycol ester of stearic acid, ethoxylated cocomonoglyceride, octyphenoxypoly(ethyleneoxy)ethanol, ethoxylatedoctylphenol, and linear alcohol, or, from among the cationic surfactants, cocohydroxyethyl imidazoline, lauryltrimethylammonium chloride, decyltrimethylammonium bromide, octyltrimethylammonium bromide, or from among the zwitterionic surfactants lauramidopropyl betaine, N-tetradecyl-N,N-dimethyl-3-ammonio-1-propane sulfonate, N-dodecyl-N,N-dimethyl-3-ammonio-1-propane sulfonate, cocoamidopropyl betaine, cocoamido sulfobetaine, N-dodecyl-N,N-dimethyl-3-ammonio-1-propane sulfonate, and N-tetradecyl-N,N-dimethyl-3-ammonio-1-propane sulfonate.

The fixation medium comprises a fixative and an osmolarity adjustment agent for providing appropriate osmolarity of the fixation medium. The osmolarity of the fixation medium is determined based on the specific non-nucleated blood cells used and required property of the analog. Suitable examples of the osmolarity adjustment agents include, but are not limited to, alkaline metal phosphate, alkaline metal chloride and alkaline metal sulfate. The fixative includes, but is not limited to, aldehyde, oxazolidine, alcohol, cyclic urea, or combinations thereof. Suitable examples include, without limitation, formaldehyde, paraformaldehyde, glutaraldehyde, diazolidinyl urea (DU), imidazolidinyl urea (IDU), dimethylol urea, dimethylol-5,5-dimethylhydantoin, 2-bromo-2-nitropropane-1,3-diol, 5-hydroxymethyl-1-aza-3,7-dioxabicyclo(3.3.0)octane, 5-hydroxypolymethyleneoxy-methyl-1-aza-3,7-dioxabicyclo(3.3.0)octane, sodium hydroxymethyl glycinate, and mixtures thereof. In a preferred embodiment, an aldehyde fixative, such as paraformaldehyde, formaldehyde, glutaraldehyde, or combinations thereof is used. The concentration of the aldehyde fixatives in the fixation medium can be in a range from about 0.1% to about 2.0%.

If the natural cell size of the non-nucleated red blood cells is larger than the size of the nucleus of a nucleated red blood cell to be simulated, the fixation medium has an osmolarity higher than the isotonic natural cellular environment to shrink the cell size during the fixing process, and to obtain a NRBC analog closely resembling the size of the nucleus of the nucleated red blood cells to be simulated. On the contrary, if the natural cell size of the non-nucleated red blood cells is smaller than the size of the nucleus of a nucleated red blood cell to be simulated, the fixation medium has an osmolarity lower than the isotonic natural cellular environment to swell the cell size during the fixing process, and to obtain a NRBC analog closely resembling the size of the nucleus of the nucleated red blood cells to be simulated.

The fixing process can be from about 4 hours to about 24 hours. Typically, the non-nucleated red blood cells are incubated in the fixation medium with gentle mixing for about 10 to about 16 hours.

One suitable example of the suspension medium includes phosphate buffered saline solution and an aqueous solution of a plasma substance. As defined herein, an aqueous solution of a plasma substance comprises an aqueous solution of a serum substance, serum substance in combination with a plasma protein, and mixtures thereof. As further defined herein, plasma protein comprises one or more of the proteins contained in plasma. Preferably, such plasma proteins include albumin, lipoproteins, globulins, fibrinogens, and mixtures thereof. These media may contain other ingredients known to those skilled in the art to confer long term stability. Example 1 provides two exemplary formulas of the suspension medium. Other examples of suitable medium are more fully described in U.S. Pat. Nos. 4,213,876, 4,299,726, 4,358,394, 3,873,467, 4,704,364, 5,320,964, 5,512,485, and 6,569,682, which are herein incorporated by reference in their entirety.

Example 1 illustrates an exemplary process of preparing the NRBC analog using horse red blood cells. Example 2 illustrates an exemplary process of preparing the NRBC analog using sheep red blood cells. The NRBC analogs produced using the process described herein are stable in the suspension medium for more than 6 months.

It has been found that the NRBC analog produced by fixing the non-nucleated animal red blood cells with the described process is resistant to the lytic reagents used for preparing the blood sample mixture for measurement of white blood cells and nucleated red blood cells on automated blood analyzers. The NRBC analog substantially maintains its size or volume under the lysing condition. When being measured in the sample mixture, the NRBC analog resembles the nucleated red blood cells of a blood sample under the lysing conditions, which are substantially at their nuclear volume. Therefore, it can be understood that although the NRBC analog is made of non-nucleated blood cells, it possesses certain properties similar to the nucleated red blood cells of a blood sample under the condition of the measurement. Different from the NRBC analogs known in the art, the NRBC analog of the present invention is substantially free of nucleic acid. In one aspect, the instant NRBC analog made of non-nucleated blood cells does not contain cellular nuclei. In another aspect, the instant NRBC analog does not contain natural or synthetic nucleic acids coated on, or chemically linked to, the surface of the cellular membrane, or infused into the cellular membrane. Therefore, it can be appreciated that the NRBC analog of the present invention can be produced using abundant non-nucleated animal red blood cells with a simple manufacturing process.

In a further embodiment, the reference control composition further includes a white blood cell component which simulates white blood cells (WBC). In the presence of a white blood cell component, a ratio between the NRBC component and the white blood cell component can be used to report the number of NRBC per 100 WBC, which is the same unit used for reporting nucleated red blood cells of a blood sample in clinical laboratories. Preferably, the white blood cell component or analog has properties similar to one major white blood cell subpopulation, such as granulocytes or lymphocytes.

Furthermore, the white blood cell component can include more than one white blood cell subpopulation component or analog, for example, two, three, four or five white blood cell subpopulation analogs to simulate white blood cell subpopulations for a differential analysis. Suitable examples of white blood cell analogs include stabilized and fixed mammalian white blood cells, and processed and/or fixed human and animal red blood cells, as known in the art. In one embodiment, the white blood cell analogs can be made from processed goose and alligator red blood cells for differential analysis using a combination of impedance and light scatter measurement, as taught in U.S. Pat. Nos. 5,320,964 and 5,512,485, which are herein incorporated by reference in their entirety. In another embodiment, the white blood cell analogs can be made from processed avian and human red blood cells for differential analysis using an impedance measurement, as taught in U.S. Pat. No. 4,704,364, which is herein incorporated by reference in its entirety. In a further embodiment, the white blood cell analogs can be made from fixed mammalian white blood cells. The mammalian white blood cells are fixed prior to lysing the red blood cells in the whole blood during the preparation of the white blood cell analogs.

Optionally, the mammalian white blood cells and red blood cells can be further treated by contacting with a lipoprotein during the process of preparing the white blood cell analogs. The contact with lipoprotein can occur prior to fixing the white or red blood cells; and it can also occur after fixing and during storage in the suspension medium, as taught in U.S. Pat. Nos. 5,320,964, 5,512,485, 6,406,915, 6,403,377, 6,399,388, 6,221,668, and 6,200,500, which are incorporated herein by reference in their entirety.

In another embodiment, the present invention provides a reference control composition which comprises the above described nucleated red blood cell component, a white blood cell component, and additionally a red blood cell component and a platelet component in the suspension medium.

The red blood cell component can be stabilized human or animal red blood cells, preferably, stabilized human red blood cells. The process of making the red blood cell component has been described in detail in U.S. Pat. Nos. 4,299,726 and 4,358,394, which are incorporated by references in their entirety. The platelet component can be stabilized human or animal platelets, or platelet analogs made from other cell types. One suitable example is using processed goat red blood cells as the platelet analog, as disclosed in U.S. Pat. Nos. 4,264,470, 4,389,490, and 4,405,719, which are incorporated by reference in their entirety.

Similar to the red blood cells of a blood sample, the stabilized human red blood cells in the reference control composition are lysed under lysing conditions normally used for preparing a blood sample for the measurement of nucleated red blood cells and white blood cells, and should not be detected during the measurement if the analyzer operates properly. The platelets of a blood sample under the lysing conditions are reduced in size; and they are either below the detection threshold for the measurement of nucleated red blood cells, or are separated from the nucleated red blood cells. The platelet analog described above simulates the response of the platelets of a blood sample under lysing conditions. Therefore, the red blood cell component and platelet component in the reference control composition further reflect the response of the control composition to the lysing reagent, as well as reaction conditions on the instrument. Hence, the reference control composition containing red blood cell and platelet components can provide further information related to instrument operating conditions.

Moreover, the reference control composition containing red blood cell and platelet analogs can also be used for red blood cell and platelet measurements, which are commonly performed together with the measurements of the white blood cells and nucleated red blood cells on an automated hematology analyzer.

Optionally, the reference control composition can further comprise a reticulocyte component for the analysis of reticulocytes. The reticulocyte component can be made using the method known in the art, for example, the methods described in U.S. Pat. Nos. 6,399,388, 6,403,377, and 6,406,915, which are herein incorporated by reference in their entirety.

Example 3 illustrates preparation of a reference control composition containing a NRBC analog made of horse red blood cells using the process described in Example 1, a single population white blood cell component, a red blood cell component and a platelet component. Example 4 further illustrates preparation of a reference control composition containing a nucleated red blood cell component of the present invention, a plurality of white blood cell subpopulation analogs, a red blood cell component, and a platelet component.

The reference control composition containing the nucleated red blood cell component of the present invention can be utilized for nucleated red blood cell measurement using various measurement methods. Example 3 illustrates a method of using the reference control composition containing a nucleated red blood cell component for the measurement of nucleated red blood cell using a DC impedance measurement, or a combination of DC and VCS measurements. The term of "VCS measurement or detection method" used herein refers to a three-dimensional measurement technology which measures the direct current (DC) and radio frequency (RF) impedances, and light scatter signals of a blood cell when it passes through a flow cell. The VCS detection method has been described in detail in U.S. Pat. No. 5,125,737, which is hereby incorporated by reference in its entirety. The method of measuring nucleated red blood cells using a combination of DC and VCS measurements has been described fully in U.S. Pat. No. 6,472,215, which is hereby incorporated by reference in its entirety.

Typically, on an automated hematology analyzer, several aliquots of a blood sample are processed separately for measurement of different blood cell subpopulations. On the Coulter GEN*S or LH750 hematology analyzer (Beckman Coulter, Inc., Fullerton, Calif.), several aliquots of a blood sample are analyzed concurrently in different analysis modes. A first aliquot of a blood sample is diluted by a blood diluent to form a first sample mixture, and red blood cells and platelets are measured by DC impedance measurement to obtain red blood cell and platelet parameters. At the same time, a second aliquot of the blood sample is mixed with a blood diluent and a first lytic reagent to form a second sample mixture, and the second sample mixture was measured by a DC impedance measurement for obtaining the white blood cell count, differentiating white blood cells into three subpopulations, and analyzing nucleated red blood cells. A third aliquot of the sample was mixed with a second lytic reagent, and subsequently mixed with a stabilizing reagent to form a third sample mixture. The third sample mixture was delivered to a flow cell and measured by the VCS detection method for differential analysis of white blood cells into five subpopulations and analysis of nucleated red blood cells.

Figure 2A:
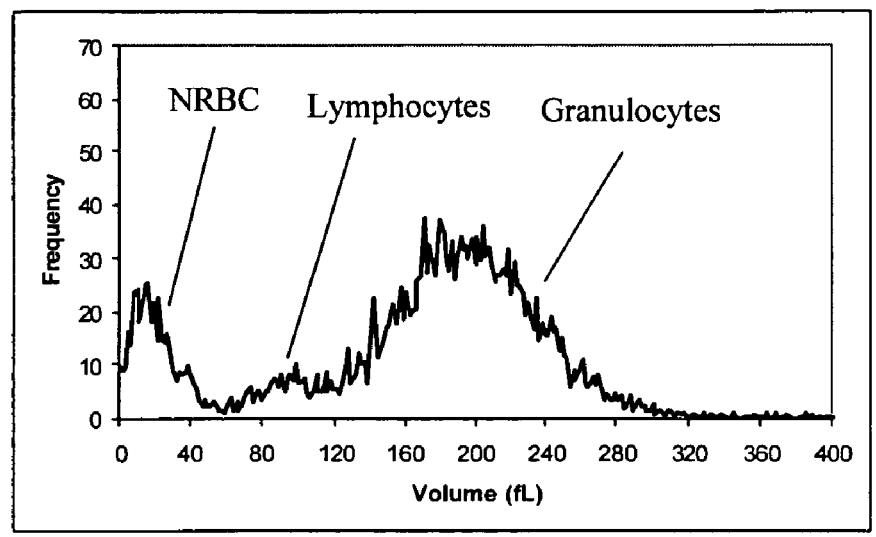
FIG. 2A shows a DC histogram of a clinical sample containing 27 NRBC/100 WBC, analyzed according to the procedure described in Example 3.

FIGS. 1A and 2A show the DC histograms obtained from the second aliquots of a normal whole blood sample and a clinical whole blood sample containing about 27 NRBC per 100 WBC, respectively, as more fully described in Example 3. As shown, the nucleated red blood cells in the clinical blood sample appeared as a distinct peak at the left-most of the histogram, while the normal blood sample had no cell population in the same region.

Figure 1B:
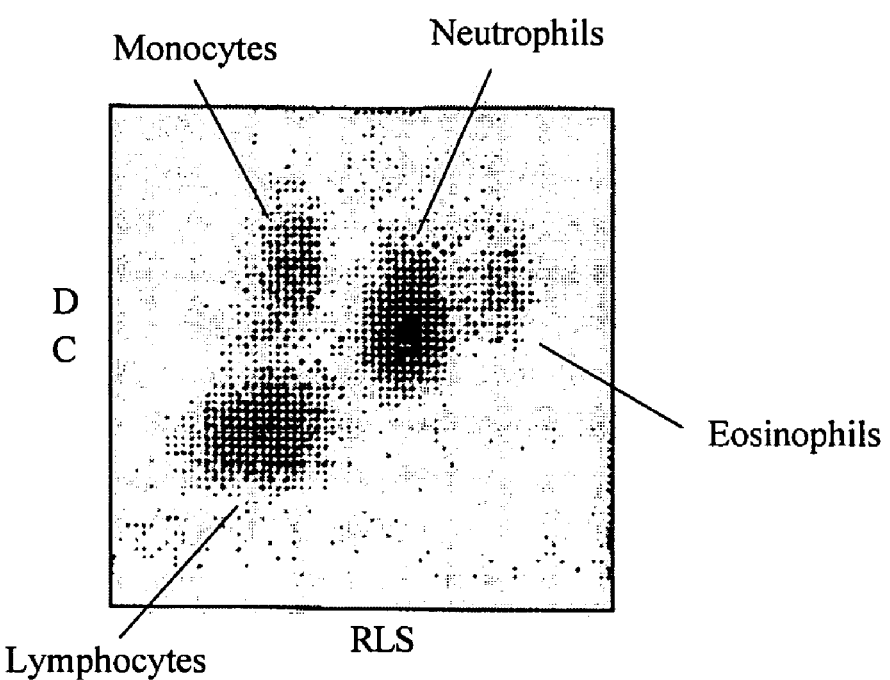
FIG. 1B shows a DC vs. RLS scattergram of the same blood sample shown in FIG. 1A, analyzed according to the procedure described in Example 3.
Figure 2B:
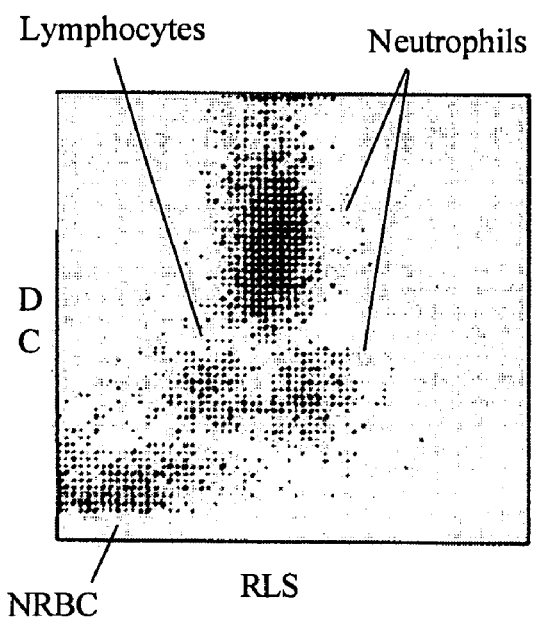
FIG. 2B shows a DC vs. RLS scattergram of the clinical sample shown in FIG. 2A, analyzed according to the procedure described in Example 3.

FIGS. 1B and 2B show DC vs. RLS scattergrams obtained from the third aliquots of the normal and clinical blood samples shown in FIGS. 1A and 2A. As shown, the nucleated red blood cells in the clinical blood sample located at the bottom left of the scattergram, while the normal blood sample had no appreciable amount of cells at the same region. It is noted that RLS is an abbreviation of the term "rotated light scatter" which is defined as a function of a medium angle light scatter signal and DC impedance signal.

Figure 3A:
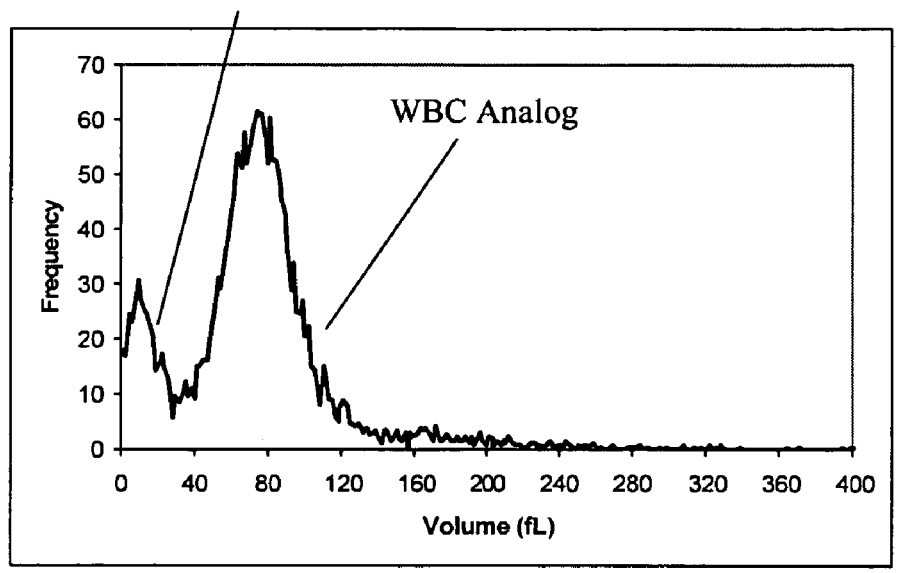
FIG. 3A shows a DC histogram of the reference control composition of Example 3, analyzed according to the procedure described in Example 3.
Figure 3B:
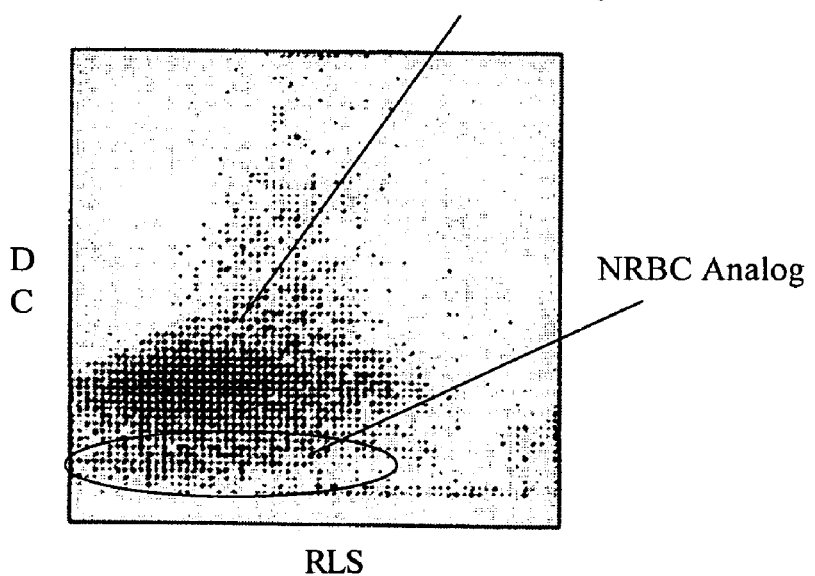
FIG. 3B shows a DC vs. RLS scattergram of the same reference control composition shown in FIG. 3A, analyzed according to the procedure described in Example 3.

FIGS. 3A and 3B show the DC histogram obtained from the second aliquot, and the DC vs. RLS scattergram obtained from the third aliquot of the reference control composition of Example 3, respectively. As shown in FIG. 3A, the NRBC analogs made of the fixed horse red blood cells located at the left-most of the histogram, which closely resembled human nucleated red blood cells. As shown in FIG. 3B, the NRBC analogs located at the bottom left of the scattergram in the same region of the human nucleated red blood cells; and the fixed goose red blood cells closely resembled human lymphocytes in both DC histogram and the DC vs. RLS scattergram. As illustrated, the reference control composition of Example 3 can be either used for a DC alone measurement, or used for a combination of DC and VCS measurement.

Although Example 3 illustrates the use of the reference control composition using DC and VCS measurement methods, since the nucleated red blood cell component of the present invention has an analog size closely resembling the size of the nucleus of the nucleated red blood cells, the reference control composition can be used with various detection methods based on the measurement of cell size. These include, but are not limited to, impedance, light scatter, and axial light loss measurements.

Low angle light scatter and axial light loss measurements have been used for measuring nucleated red blood cells. The term of "low angle light scatter" refers to the light scatter signals detected in less than 10° from the incident light, which is also commonly referred to as forward light scatter.

Axial light loss (ALL, also known as forward extinction) is generally the decrease in light energy due to a particle passing through a beam of incident light and being detected by a photo-detector. When the beam of incident light strikes a particle, the light is either scattered or absorbed, both of which remove energy from the incident light and the incident beam is attenuated. This attenuation is referred to as extinction. When viewed along the axis of the beam of incident light, it is referred to as axial light loss. Generally, ALL signals are detected at an angle from about 0° to about 1° from the incident light. In a preferred embodiment of the present invention, ALL signals are collected in a circular area less than about 0.5° from the incident light axis. ALL signals are strongly influenced by the size of the cell. Since axial light loss measurement measures the loss of energy from the beam of incident light, whereas low angle light scatter measurement measures the increase in light, different electronic circuitries are required for measuring these two different optical properties.

One suitable example of the measurement method and instrumentation, with which the reference control composition of the present invention can be utilized as a reference control for the measurement of nucleated red blood cells, has been described in detail in U.S. Pat. Nos. 5,874,310 and 5,917,584, which are herein incorporated by reference in their entirety. More specifically, the measurement of the nucleated red blood cells is performed by measuring two angles of light scatter signals. In one embodiment, the two angles of light scatter signals are both low angle light scatter signals which are detected in less than 10°, preferably from about 0° to about 4°, from the incident light. In another embodiment, the first light scatter signal is a low angle light scatter signal; and the second light scatter signal is a medium, or a right-angle light scatter signal. Furthermore, the measurement of the nucleated red blood cells can also be performed by measuring light scatter and DC impedance signals.

A further suitable example of the measurement method and instrumentation, with which the reference control composition of the present invention can be utilized as a reference control for the measurement of nucleated red blood cells, has been described in detail in the co-pending patent application Ser. Nos. 11/048,086 and 11/338,229, which are herein incorporated by reference in their entirety. More specifically, the methods described in patent application Ser. No. 11/048,086 measures the nucleated red blood cells by measuring axial light loss and low angle light scatter signals; axial light loss and DC impedance signals; or axial light loss, DC impedance, and low angle light scatter signals. The methods described in patent application Ser. No. 11/338,229 measures the nucleated red blood cells by measuring axial light loss, DC impedance, medium angle light scatter signals; axial light loss, low angle and medium angle light scatter signals; or axial light loss, DC impedance, low angle and medium angle light scatter signals. The low angle light scatter signals are preferably measured from about 1° to 7°, and the medium angle light scatter signals are preferably measured from about 20° to about 45°.

Different from existing reference controls for NRBC measurement, which all require using nucleated blood cells for preparing the NRBC component, the reference control composition of the present invention does not need to use nucleated blood cells. Instead, those readily available and abundant non-nucleated red blood cells can be utilized for making the NRBC component.

Example 4 shows a reference control composition containing a NRBC component, multiple white blood cell subpopulation analogs, red blood cell and platelet components. In addition to red blood cell, platelet and NRBC measurements, this reference control composition can be further used for differential analysis of white blood cells to five subpopulations using VCS measurement.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

Nucleated Red Blood Cell Component Made of Horse Red Blood Cells

Phosphate Buffered Saline Solution (PBS)

| Component | Amount (g/l) |
|---|---|
| Sodium dihydrogenphosphate: | 0.2 g |
| Disodium hydrogenphosphate 7H$_2$O: | 2.0 g |
| Sodium azide: | 0.1 g |
| Sodium chloride: | 9.4 g |
| Qs to 1 liter with distilled water: | pH approximately 7.4 osmolarity 315 to 345 mOsm/kg H$_2$O |

Analog Fixation Medium 1

| Component | Amount (g/l) |
|---|---|
| Disodium hydrogenphosphate 7H$_2$O: | 2.0 g |
| Sodium dihydrogenphosphate: | 0.2 g |
| Sodium chloride | 8.0 g |
| Glutaraldehyde (25%) | 40 ml |
| Qs to 1 liter with distilled water: | pH approximately 7.4 osmolarity 285 mOsm/kg H$_2$O |

Suspension Medium 1

| Component | Range (g/l) | Preferred Range (g/l) |
|---|---|---|
| Xanthine compound | 1-10 | 2-7 |
| Adenosine monophosphate | 0.1-1.0 | 0.2-0.8 |
| Inosine | 0.1-1.0 | 0.2-0.8 |
| pH adjusting agents sufficient to obtain | pH 5.8-6.8 | pH 6.0-6.5 |
| Osmolarity adjusters sufficient to obtain | 200-400 mOsm | 250-350 |
| Preservative | effective amount | 2.0-6.0 |
| Qs to 1 liter with distilled water | | |

Suspension Medium 2

| Component | Preferred Range (g/l or ml/l) |
|---|---|
| Propyl paraben | 0.3 to 1.0 g |
| Methyl paraben | 0.5 to 1.0 g |
| Procaine hydrochloride | 0.1 to 0.5 g |
| Deoxycholic acid | 0.1 to 0.9 g |
| Lactose | 10.0 to 50.0 g |
| Actidione | 0.1 to 0.6 g |
| Trisodium citrate dehydrate | 3.0 to 8.0 g |
| Citric acid monohydrate | 0.3 to 0.9 g |
| Sodium dihydrogenphosphate monohydrate | 0.8 to 2.5 mg |
| Phenergan hydrochloride | 0.1 to 1.0 g |
| Colistimethate, sodium | 0.2 to 0.9 g |
| Penicillin G., sodium | $0.5 \times 10^6$ to $3 \times 10^6$ units |
| Kanamycin sulfate | 0.2 to 0.8 g |

-continued

Suspension Medium 2

| Component | Preferred Range (g/l or ml/l) |
|---|---|
| Neomycin sulfate | 0.2 to 1.0 g |
| 5'-AMP | 0.4 to 1.0 g |
| Adenine | 0.2 to 0.8 g |
| Inosine | 0.4 to 1.0 g |
| Dihydrostreptomycin sulfate | 0.2 to 1.0 g |
| Tetracycline hydrochloride | 0.2 to 1.0 g |
| 30% Bovine albumin | 100 to 350 ml |
| Qs to 1 liter with distilled water | |

Process steps for preparing the NRBC analog using horse red blood cells:

1. Collect 50 ml whole blood from a horse in an anticoagulant containing container. Centrifuge the horse whole blood and remove the top layer that includes white blood cells, platelets, and plasma.

2. Wash the packed horse red blood cells three times with the phosphate buffered saline solution (PBS), and re-suspend washed packed cells in the residual amount of PBS. The cell washing step was a series of centrifugations at 1200 rpm for 15 minutes, followed by removal of the supernatant and re-suspension of the packed cells with PBS.

3. Add 1 ml of packed horse red blood cells into a test tube containing 49 ml of Analog Fixation Medium 1, and mix well by inversion to form a cell processing suspension.

4. Place the test tube on a roller and mix at a slow speed for overnight at room temperature.

5. Wash the processed cells three times with PBS, as described in step (2).

6. Re-suspend the processed cells in Suspension Medium 1 or 2 to form a NRBC reference control composition for analysis on a blood analyzer.

EXAMPLE 2

Nucleated Red Blood Cell Component Made of Sheep Red Blood Cells 50 ml whole blood was collected from a sheep and processed with the same process steps described in Example 1, except that in step 3 Analog Fixation Medium 2 shown below was used. The processed sheep red blood cells were re-suspended in Suspension Medium 1 to form another NRBC reference control composition.

Analog Fixation Medium 2

| Component | Amount (g/l) |
|---|---|
| Disodium hydrogenphosphate 7H$_2$O: | 2.0 g |
| Sodium dihydrogenphosphate: | 0.2 g |
| Sodium chloride | 9.4 g |
| Glutaraldehyde (25%) | 40 ml |
| Qs to 1 liter with distilled water: | pH approximately 7.4 osmolarity 320 mOsm/kg H$_2$O |

EXAMPLE 3

Reference Control Composition Containing a Nucleated Red Blood Cell Component, a White Blood Cell Component, and Red Blood Cell and Platelet Components Preparation procedure:
1. Provide a predetermined volume of Suspension Medium 1 of Example 1.
2. Add a predetermined amount of stabilized human red blood cells in the medium. The stabilized human red blood cells were processed following the procedure described in U.S. Pat. Nos. 4,299,726 and 4,358,394.
3. Add a predetermined amount of platelet component in the suspension medium containing the stabilized human red blood cells. The platelet component is made of fixed goat red blood cells following the procedure described in U.S. Pat. Nos. 4,264,470, 4,389,490, and 4,405,719.
4. Add a predetermined amount of a white blood cell component made of fixed goose red blood cells into the suspension medium containing the stabilized human red blood cells and the platelet component.
5. Add a predetermined amount of fixed horse red blood cells of Example 1 into the suspension medium containing the stabilized human red blood cells, platelet component, and white blood cell component.
6. Mix the formed reference control composition gently.

The cell concentrations of the red blood cell, white blood cell and platelet components were prepared to simulate the corresponding cell concentrations of a human whole blood sample. The cell concentration of the nucleated red blood cell component was prepared to simulate clinical samples containing certain level of nucleated red blood cells, preferably in a range of 1 to 50 NRBC per 100 WBC.

The reference control composition obtained from the above-described process was analyzed on a Coulter LH750 hematology analyzer (manufactured by Beckman Coulter, Inc., Fullerton, Calif.). The Coulter LH750 hematology analyzer has a RBC bath using three non-focused flow apertures and a DC-impedance detector for measuring red blood cells; a WBC bath using three non-focused flow apertures and a DC-impedance detector for measuring white blood cell count, and for differentiating white blood cell into three subpopulations and analysis of nucleated red blood cells; and a flow cell with a VCS detection system for differentiating white blood cells into five subpopulations. The VCS detection system measures DC impedance, radio frequency impedance, and medium angle light scatter signals of a cell passing through the flow cell.

A blood sample, or a reference control composition, was aspirated by the Coulter LH750 hematology analyzer. A first aliquot of 1.6 µl of the sample was diluted by an isotonic blood diluent, LH700 Series Diluent, with a dilution ratio of 6250:1 to form a first sample mixture. The first sample mixture was drawn through a set of three apertures by a vacuum source. Each blood cell was measured, as it passed through the apertures by the DC impedance detector to obtain red blood cell parameters. A second aliquot of 28 µl of the sample was diluted with 6 ml of the LH700 Series Diluent, then mixed with 1 ml of a first lytic reagent, Lyse S® III diff to form a second sample mixture. The second sample mixture was drawn through a set of three apertures by a vacuum source, and measured for obtaining white blood cell count, differentiating white blood cell into three sub-populations and analyzing nucleated red blood cell. A third aliquot of 34 µl of the sample was mixed with 540 µl of a second lytic reagent, Erythrolyse® II, to lyse red blood cells and subsequently mixed with 218 µl of a stabilizing reagent, Stabilyse, to form a third sample mixture. The third sample mixture was delivered to a flow cell for differential analysis of white blood cells into five subpopulations and analysis of nucleated red blood cells. The measurement was performed at a temperature in a range of about 18° to about 28° C. The data obtained from measurements of the second aliquot and the third aliquot samples were analyzed to report the nucleated red blood cells. All reagents described above were products of Beckman Coulter, Inc.

FIG. 1A shows a DC histogram obtained from the second aliquot of a normal whole blood sample analyzed according to the procedure described above. As shown, three white blood cell subpopulations distributed in a range of 0 to 400 fl, and no cell population appeared on the left of the white blood cells. FIG. 1B shows a DC vs. RLS scattergram obtained from the third aliquot of the same blood sample. As shown, no appreciable amount of cells located at the bottom of the scattergram.

FIG. 2A shows a DC histogram obtained from the second aliquot of a clinical whole blood sample which contained about 27 NRBC per 100 WBC, analyzed according to the procedure described above. As shown, the nucleated red blood cells appeared as a distinct peak at the left-most of the histogram. FIG. 2B shows a DC vs. RLS scattergram obtained from the third aliquot of the same clinical sample. As shown, the nucleated red blood cells located at the bottom left of the scattergram.

FIGS. 3A and 3B are the DC histogram and the DC vs. RLS scattergram, respectively, obtained from the second and third aliquots of the reference control composition described above. As shown, the fixed horse red blood cells appeared as a distinct peak at the left-most of the DC histogram, and located at the bottom left of the DC vs. RLS scattergram; therefore, they closely resembled human nucleated red blood cells in both DC and DC vs. RLS measurements. On the other hand, the fixed goose red blood cells resembled human lymphocytes.

EXAMPLE 4

Hematology Reference Control Composition Containing a NRBC Component, Multiple White Blood Cell Subpopulation Analogs, Red Blood Cell and Platelet Components The procedure for making this reference control composition is essentially the same as the procedure described above in Example 3, except that in step 4 predetermined amounts of multiple white blood cell subpopulation analogs were added into the suspension medium containing the stabilized human red blood cells, platelet component and the NRBC component made in Example 1 or 2.

The multiple white blood cell subpopulation analogs were prepared following the procedures described in U.S. Pat. Nos. 5,320,964 and 5,512,485. The reference control composition can be stored for a time period in excess of 45 days.

This reference control composition can be used for the analysis of nucleated red blood cells using the combination of DC impedance measurement and VCS measurement, which is described in detail in U.S. Pat. No. 6,472,215.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A reference control composition containing a nucleated red blood cell component comprising:
    (a) a nucleated red blood cell component made of a fixed non-nucleated blood cell for simulating a nucleated red blood cell of a blood sample, wherein the cellular membrane of said non-nucleated blood cell is not coated or chemically linked to a biopolymer; and
    (b) a suspension medium suitable for delivering said component to a blood analyzer for measurement of said nucleated red blood cell.

2. The reference control composition of claim 1, wherein said non-nucleated blood cell has a natural cell size substantially similar to a size of nucleus of said nucleated red blood cell of said blood sample.

3. The reference control composition of claim 2, wherein said non-nucleated blood cell comprises equine, ovine, bovine, feline, canine, porcine red blood cells, or combinations thereof.

4. The reference control composition of claim 2, wherein said fixed non-nucleated blood cell is substantially free of nucleic acid.

5. The reference control composition of claim 1 further comprising a white blood cell component.

6. The reference control composition of claim 1 further comprising a red blood cell component.

7. The reference control composition of claim 1 further comprising a platelet component.

8. The reference control composition of claim 1 further comprising a reticulocyte component.

9. A method of making a reference control composition containing a nucleated red blood cell component comprising the steps of:
    a) providing a non-nucleated blood cell which has a natural cell size substantially similar to a size of a nucleus of a nucleated red blood cell to be measured, wherein the cellular membrane of said non-nucleated blood cell is not coated or chemically linked to a biopolymer;
    b) fixing said non-nucleated blood cell with a fixation medium; and
    c) suspending fixed non-nucleated blood cell obtained from step (b) in a suspension medium to form a reference control composition.

10. The method of claim 9, wherein said non-nucleated blood cell comprises equine, ovine, bovine, feline, canine, porcine red blood cells, or combinations thereof.

11. The method of claim 9, wherein said fixed non-nucleated blood cell is substantially free of nucleic acid.

12. The method of claim 9, wherein said fixation medium comprises a fixative and an osmolarity adjustment agent.

13. The method of claim 9 further comprising contacting said non-nucleated blood cell with a sphering reagent to sphere said non-nucleated blood cell prior to step (b).

14. The method of claim 9 further comprising adding a white blood cell component, a red blood cell component, a platelet component, a reticulocyte component, or combinations thereof, into said suspension medium.

15. A method of using a reference control composition containing a nucleated red blood cell component comprising the steps of:
    a) providing a reference control composition containing a nucleated red blood cell component made of a fixed non-nucleated blood cell for simulating a nucleated red blood cell of a blood sample to be measured, wherein the cellular membrane of said non-nucleated blood cell is not coated or chemically linked to a biopolymer;
    b) providing a blood analyzer adapted for measurement of the nucleated red blood cell of the blood sample;
    c) analyzing said reference control composition on said blood analyzer, and measuring said nucleated red blood cell component; and
    d) reporting said nucleated red blood cell component in said reference control composition.

16. The method of claim 15, wherein said measuring said nucleated red blood cell component is performed by measuring a DC impedance signal.

17. The method of claim 15, wherein said measuring said nucleated red blood cell component is performed by measuring two angles of light scatter signals.

18. The method of claim 17, wherein said two angles of light scatter signals are low angle light scatter signals detected in less than 10°.

19. The method of claim 17, wherein said two angles of light scatter signals are a low angle light scatter signal, and a medium angle or a right-angle light scatter signal.

20. The method of claim 15, wherein said measuring said nucleated red blood cell component is performed by measuring DC impedance and light scatter signals.

21. The method of claim 15, wherein said measuring said nucleated red blood cell component is performed by measuring axial light loss and DC impedance signals.

22. The method of claim 15, wherein said measuring said nucleated red blood cell component is performed by measuring axial light loss and light scatter signals.

23. The method of claim 22, wherein said light scatter signal is a low angle light scatter signal.

24. The method of claim 22, wherein said light scatter signal is a medium angle light scatter signal.

25. The method of claim 15, wherein said measuring said nucleated red blood cell component is performed by measuring a first DC impedance signal of a first aliquot of said blood sample and measuring a second DC impedance signal, a radio frequency impedance signal, and a light scatter signal of a second aliquot of said blood sample.

* * * * *